US010357350B2

(12) United States Patent
Astani-Matthies et al.

(10) Patent No.: US 10,357,350 B2
(45) Date of Patent: Jul. 23, 2019

(54) SURGICAL IMPLANT

(71) Applicant: JOHNSON & JOHNSON MEDICAL GMBH, Norderstedt (DE)

(72) Inventors: Aida Astani-Matthies, Kaltenkirchen (DE); Thorsten Deichmann, Aachen (DE); Dajana Kaiser, Hamburg (DE); Andrea Hennemann, Sievershutten (DE); Burkhard Peters, Wattenbek (DE)

(73) Assignee: Johnson & Johnson Medical GmbH, Norderstedt (DE)

( * ) Notice: Subject to any disclaimer, the term of this patent is extended or adjusted under 35 U.S.C. 154(b) by 142 days.

(21) Appl. No.: 14/060,694

(22) Filed: Oct. 23, 2013

(65) Prior Publication Data
US 2014/0128891 A1 May 8, 2014

(30) Foreign Application Priority Data

Nov. 2, 2012 (DE) .......................... 10 2012 021 547

(51) Int. Cl.
*A61F 2/00* (2006.01)

(52) U.S. Cl.
CPC .... *A61F 2/0063* (2013.01); *A61F 2230/0063* (2013.01); *Y10T 29/49826* (2015.01)

(58) Field of Classification Search
CPC ...... A61F 2230/0063; A61F 2230/0067; A61F 2/0063; A61F 2/01; A61F 2/30723; A61F 2002/30247; A61B 17/0057; A61B 17/12172; A61B 17/12168; D10B 2509/08; A61M 27/008; B65D 75/20

USPC .......................................... 606/213
See application file for complete search history.

(56) References Cited

U.S. PATENT DOCUMENTS

| 4,900,632 | A | * | 2/1990 | McGrath | D04D 7/10 223/46 |
|---|---|---|---|---|---|
| 5,215,791 | A | * | 6/1993 | Davignon | D04D 7/10 223/46 |
| 5,249,682 | A | * | 10/1993 | Transue | 206/438 |
| 6,616,685 | B2 | | 9/2003 | Rousseau | |
| 6,712,836 | B1 | * | 3/2004 | Berg | A61B 17/0057 606/213 |

(Continued)

FOREIGN PATENT DOCUMENTS

| CN | 101112335 A | 1/2008 |
|---|---|---|
| CN | 101573084 A | 11/2009 |

(Continued)

OTHER PUBLICATIONS

Definition of Areal by the Free Dictionary, accessed on Sep. 30, 2016, <http://www.thefreedictionary.com/areal>.*
Search Report, WO2014/067608, dated Dec. 17, 2013.

*Primary Examiner* — David C Eastwood
*Assistant Examiner* — Mohamed G Gabr

(57) ABSTRACT

A surgical implant adapted for repairing a tissue or muscle wall defect comprises an areal, flexible basic structure which defines a primary region and at least one arm starting from the primary region and having a free end and an end area extending up to the free end. The arm is folded back and fixed (e.g. welded, sutured or glued), in its end area, to the primary region of the basic structure. Preferably, the basic structure is made from one piece and comprises a mesh.

14 Claims, 4 Drawing Sheets

(56) References Cited

U.S. PATENT DOCUMENTS

Figure 1A:
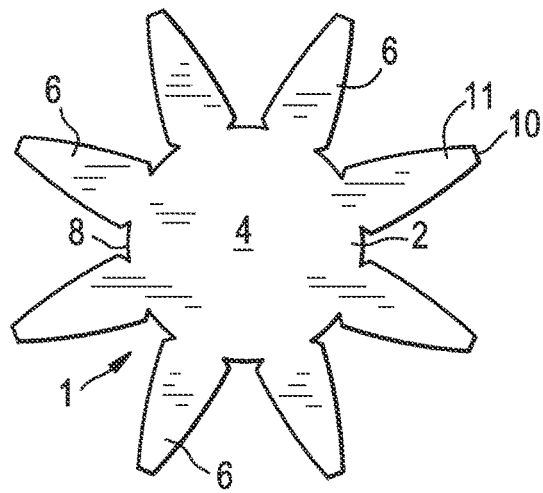

| | | | | |
|---|---|---|---|---|
| 2008/0147200 A1* | 6/2008 | Rousseau | ............ | A61F 2/0063 |
| | | | | 623/23.75 |
| 2008/0287970 A1* | 11/2008 | Amato et al. | ................ | 606/151 |
| 2011/0178608 A1 | 7/2011 | Rosseau et al. | | |
| 2013/0138124 A1* | 5/2013 | Criscuolo | ............ | A61F 2/0063 |
| | | | | 606/151 |
| 2014/0316428 A1* | 10/2014 | Golan | ............... | A61B 17/3207 |
| | | | | 606/128 |
| 2015/0351887 A1* | 12/2015 | Peters | ............... | A61B 17/0057 |
| | | | | 606/151 |

FOREIGN PATENT DOCUMENTS

| | | | | |
|---|---|---|---|---|
| EP | 0614650 A2 | 2/1994 | | |
| EP | 0888756 A2 | 1/1999 | | |
| FR | 2778554 A1 | 11/1999 | | |
| WO | WO97/45068 A1 | 12/1997 | | |
| WO | WO 2011069025 A1 * | 6/2011 | ............ | A61B 17/22 |

* cited by examiner

SURGICAL IMPLANT

CROSS REFERENCE TO RELATED APPLICATIONS

This application claims priority from German Patent Application DE 102012021547.9 filed Nov. 2, 2012 the disclosure of which is hereby incorporated by reference in its entirety.

The invention relates to a surgical implant adapted for repairing a tissue or muscle wall defect, in particular for repairing an inguinal hernia, and to a method of manufacturing such implant.

The repair of inguinal hernias is one of the most commonly performed surgical procedures. Various prosthetic materials, typically porous to allow for tissue in-growth, have been provided in a variety of combinations, forms and shapes. The repair of inguinal hernias is often achieved by implanting a mesh plug into the hernia defect. Various materials have been discussed for use as prosthetic plugs. Polypropylene is most often used in the form of a knitted mesh fabric to create the desired shapes.

Many of the commercially available plugs comprise an outer shell (usually made of mesh material) with a separate "filler" material attached to the inside of the outer shell. The filler serves as a means to grasp and position the plug during a surgical procedure. Moreover, the filler, in conjunction with the outer shell, enables tissue in-growth to occur over time.

EP 0 614 650 A2 discloses an implantable prosthesis for muscle or tissue wall repairs comprising a mesh of knitted polypropylene monofilaments. An outer shell made from the mesh material is cone-like (and fluted). Moreover, multiple inner layers of mesh material are provided, which are located in the outer shell and attached in the tip area of the cone configuration. A similar implant is known from WO 97/45068 A1.

CN 101112335 A describes an embeddable multipurpose external hernia-remedying slice comprising a substrate and a plurality of petals arranged on the upper surface of the substrate. The distal ends of the petals are free, whereas the proximal ends are fixed to the center of the substrate. A plurality of reinforcement ribs can be arranged on the upper surface of the substrate.

EP 0 888 756 A2 discloses a surgical implant for hernioplasty made of polypropylene mesh material, in which an a real base and a protrusion serving as a plug are joined by stiches.

U.S. Pat. No. 6,616,685 B shows an implant for repairing a tissue or muscle wall defect comprising a plurality of petals, which are connected to one another at a common point defining the center of the implant. Since the petals are flexible, the implant is able to adapt to a tissue defect when it is inserted therein, wherein some of the petals can serve as a filler.

Generally, separate fabrication steps are required to attach the filler to the inside of the outer shell. Eliminating the filler material would be one way to simplify the manufacture; however, this would also eliminate the benefits and functionality of having a filler material.

It is the object of the invention to provide a surgical implant adapted for repairing a tissue or muscle wall defect, which has the advantages of the prior art implants discussed before, but which can be manufactured in an easier and less expensive way.

This object is achieved by a surgical implant having the features of claim 1. Advantageous versions of the implant follow from the dependent claims.

The surgical implant according to the invention is adapted for repairing a tissue or muscle wall defect, in particular an inguinal hernia. The implant (implantable prosthesis, plug) comprises an a real, flexible basic structure which defines a primary region and at least one arm starting from the primary region and having a free end and an end area extending up to the free end. The arm is folded back and fixed, in its end area, to the primary region of the basic structure.

The term "folded back" is to be understood in a general sense. It is not to imply the presence of a fold line, but rather means that the arm is led back to the primary region, e.g. in a smoothly curved shape or a loop, so that it can be fixed or attached to the primary region. In this way, the arm forms a three-dimensional structure serving as a filler or part of a filler.

In advantageous embodiments of the invention, a plurality of arms starts from the primary region. In this way, the primary region is generally located in the center area of the basic structure, and the arms form a kind of three-dimensional filler. The arms can have different lengths. It is also possible that at least one additional arm starts from the primary region and is not fixed to the primary region. The implant can be rotationally symmetric with respect to rotations by an angle $\alpha$ about an axis running transversely through the primary region, wherein $n \cdot \alpha = 360°$ and $n \geq 2$. Preferably, this axis of rotation is running perpendicularly with respect to a plane generally aligned in parallel to the primary region of the basic structure.

Generally, the implant according to the invention can be optimized in size and shape, depending on the application in question. The end areas of the arms, after folding back, can be easily fixed to the primary region of the basic structure, e.g. by welding, suturing and/or gluing, e.g. in a center area, in a peripheral area or in an intermediate area between the center area and the peripheral area of the primary region. It is possible to fix different arms at different distances from the center of the primary region. By varying the size and shape of the primary region, the size, length and shape of the arms, the number of arms, or the position where a respective arm is fixed to the primary region, the implant can be designed in many different forms. The folded back arms serve as a filler, which fills the defect to be repaired by the implant and which facilitates the handling during surgery because the implant can be grasped at such filler by a gripping instrument.

In advantageous embodiments of the invention, the basic structure comprises a mesh. The basic structure can also comprise a composite structure, in which at least one additional layer is added to the mesh, e.g. a film.

The mesh of the basic structure is preferably macroporous with typical pore dimensions of greater than 0.5 mm, which supports good tissue integration. Other pore sizes are conceivable as well, however. The mesh can be provided in any kind known in the art, e.g., warp-knitted or weft-knitted or crochet-knitted or woven. A design as perforated film or foil is also conceivable. Any filaments of the mesh may be bio-absorbable or non-absorbable, depending on the material. The filaments can be designed as mono-filaments or as multifilaments. Tape yarns and drawn film tapes are conceivable as well. Any blends, mixtures or composites of materials and de signs are also possible. Moreover, the filaments can be coated.

Examples for non-absorbable materials are polypropylene ("Prolene") as well as blends of polyvinylidene fluoride and copolymers of vinylidene fluoride and hexafluoropropene ("Pronova"). Examples for absorbable materials are copolymers of glycolide and lactide (in particular in the ratio 90:10, "Vicryl"), poly-p-dioxanone ("PDS"), and copolymers of glycolide and ε-caprolactone ("Monocryl"). The indicated designations are trademarks used by the applicant. Other materials suitable for the use with surgical implants are known in the art as well.

Examples for meshes comprised in the basic structure are "Vypro" and "Vypro II" meshes (containing multifilaments of "Vicryl" and polypropylene), "Ultrapro" meshes (containing monofilaments of "Monocryl" and polypropylene) and soft "Prolene" meshes (containing polypropylene). Again, the indicated designations are trademarks used by the applicant.

As already mentioned, one or more additional layers may be added to the mesh to make it a composite structure. The additional layers may include, e.g. bio-absorbable films, non-absorbable films, and/or oxidized regenerated cellulose. By means of a film, e.g., tissue in-growth can be controlled, and a film can serve as a barrier for adhesion and a means for tissue separation. For example, the mesh of the basic structure can be covered from one or both sides with a polymeric film structure, which is absorbable or permanent and can additionally provide a barrier for adhesion.

Examples for meshes having an additional film layer are "Physiomesh" meshes and "Proceed" meshes; these designations are trademarks used by the applicant. If a "Proceed" mesh comprising one layer of oxidized regenerated cellulose (ORC) is used, the ORC layer should be placed on the outer face of the implant, i.e. that face primarily coming into contact with bodily tissue.

In advantageous embodiments of the invention, the basic structure is made from one piece, e.g. from a pre-cut mesh or composite structure. It is also conceivable, however, that the arm or arms and the primary region of the basic structure are formed from separate parts, wherein the arm or arms are attached to the material of the primary region in a first step and thereafter folded back and fixed in a second step. It is generally possible that the material or structure of the basic structure varies over its area, depending on the location of the area in question in the implant.

The primary region of the basic structure can comprise a permanent curvature, e.g. formed as a dome-like protrusion. Such curvature or dome-like protrusion stabilizes the primary region. It is preferably provided in the center area of the primary region and can be made by thermo-forming. A thermo-forming process can result in a stiffening of the material so that the protrusion is able to prevent a gripping instrument from penetrating the basic structure. The term "dome-like" is to be understood in a general sense, which includes curved and also flattened (e.g. trapezoidal) profiles, as viewed in a longitudinal section of the protrusion. The profile of the protrusion should be atraumatic in order to prevent injury when inserting the implant during surgery.

In advantageous embodiments of the surgical implant according to the invention, at least one reinforcement element is attached to the basic structure.

For example, a reinforcement element can be formed as a film strip or a pattern of film strips of the resorbable material poly-p-dioxanone ("PDS"), which is laminated to the basic structure. Ribs or a pattern of ribs are conceivable as well, wherein a rib is generally less flat than a strip. Preferably, the reinforcement elements are flexible and are attached to the sheet of the basic structure early in the manufacturing process. Another suitable material for reinforcement elements is Polyglecaprone 25 ("Monocryl"). If the reinforcement elements are made from resorbable material, they may disintegrate and leave a more flexible or softer residual implant.

The reinforcement elements strengthen and stiffen the implant where required. For example, reinforcement elements arranged concentrically with respect to a center of the primary region and/or arranged radially with respect to a center of the primary region can be laminated to one of the faces of the basic structure (e.g. on its outer face, wherein "outer" refers to the three-dimensional shape after folding the arms) to provide improved resilience plug properties for better matching of the implant to the defect margins. Further, by using reinforcement elements attached to the basic structure, the grasping and handling of the implant with an instrument for placement and positioning can be facilitated. At the same time, the reinforcement elements can also operate as a penetration protection preventing that a surgeon's instrument penetrates through the, e.g., macro-porous mesh of the basic structure, which could lead to injuries of surrounding tissue.

Moreover, the reinforcement elements or at least one of the reinforcement elements may be colored. In this way, the visibility of the whole implant in the area of surgery can be enhanced, the implant can be more easily oriented, and the grasping and general handling of the implant can be facilitated. For example, the center area of the implant can be marked by colored reinforcement elements. A suitable dye is, e.g., D&C violet No. 2.

Generally, the surgical implant according to the invention provides many advantages. It can be easily produced at relatively low cost, e.g. as a light-weight structure with low foreign body sensation and causing no or little chronic pain, but nevertheless having sufficient strength. During surgery, the implant requires minimal manipulation of anatomic structures only and, as a rule, no preperitoneal mobilization. Compared to traditional plug techniques (according to Rutkow), little training is required for working with the implant. Implantation tends to be fast and positioning easy. The foldedback arms provide a convenient grasping and handling help for placing and positioning the implant into the defect by means of a surgical instrument, wherein the tip of the instrument tends to be protected from penetrating the implant and causing injury. Generally, the volume of the defect is filled by the implant, which is flexible. Depending on the desired application and the materials used, the implant can be fully or partially bio-degradable.

The surgical implant can be used to repair defects of different sizes. It is possible to fix the implant at the margins of the defect, e.g. by suturing, wherein longer arms (greater loops) can be, in general, handled more easily. Generally, the implant can be used in the pre-peritoneal space as well as in the intra-peritoneal space (abdomen). Other possible uses relate to the repair of ventral hernia defects, umbilical and incisional hernia defects, etc.

Some surgeons prefer to place, after inserting the surgical implant described so far into a hernia defect, a piece of a separate surgical mesh on top of the implant or the bodily tissue in the area of the implant, respectively. To this end, a kit is provided which comprises a surgical implant as described before plus a separate surgical mesh, which is adapted to be placed on top of the tissue or muscle wall defect after the surgical implant has been applied. This separate surgical mesh can be pre-shaped to an appropriate size and/or can be trimmed to the desired size, if required. Preferably, the material of the separate surgical mesh is the same as that of a mesh in the basic structure. The separate surgical mesh can also comprise a composite structure.

In a method of manufacturing a surgical implant according to the invention, a flexible basic structure is provided and the arm or arms are folded back and fixed, in its or their end areas, to the primary region of the basic structure, e.g. by welding, suturing or gluing.

In the following, the invention is described in further detail by means of examples. The drawings show in FIG. 1 in parts (a), (b), (c) and (d) several views of an embodiment of the surgical implant according to the invention, i.e. in part (a) a plan view of a basic structure, in part (b) the basic structure after forming a protrusion in its center area, in part (c) a longitudinal section through the protrusion, and in part (d) a three-dimensional view of the implant after folding the basic structure, FIG. 2 a three-dimensional view of a variant of the embodiment of FIG. 1, which comprises reinforcement elements, FIG. 3 a three-dimensional view of a another variant of the embodiment of FIG. 1, which comprises arms having different lengths, FIG. 4 in parts (a), (b) and (c) several views of another embodiment of the surgical implant according to the invention, i.e. in part (a) a plan view of a basic structure, in part (b) a three-dimensional view of the implant after folding a variant of the basic structure, and in part (c) a three-dimensional view after further forming the implant, and FIG. 5 in parts (a) and (b) views of another embodiment of the surgical implant according to the invention, i.e. in part (a) a plan view of a basic structure and in part (b) a three-dimensional view of the implant after folding the basic structure.

FIG. 1 illustrates a first embodiment of a surgical implant, which is designated by reference numeral 1.

In FIG. 1(a), a basic structure 2 is shown in plan view. The basic structure 2 comprises a primary region 4 in its center area and a total of eight arms 6 starting from the periphery 8 of the primary region 4. Each arm 6 has a free end 10 and, adjacent to its free 10, an end area 11.

The basic structure 2 is a real, i.e. made of relatively thin material, and flexible. In the embodiment, it comprises a surgical mesh, e.g. a "Vypro II" mesh (see above), which includes multifilaments of "Vicryl" (absorbable) and polypropylene (non-absorbable). Moreover, in the embodiment, the basic structure 2 is made from one piece, e.g. by die-cutting.

Figure 1B:
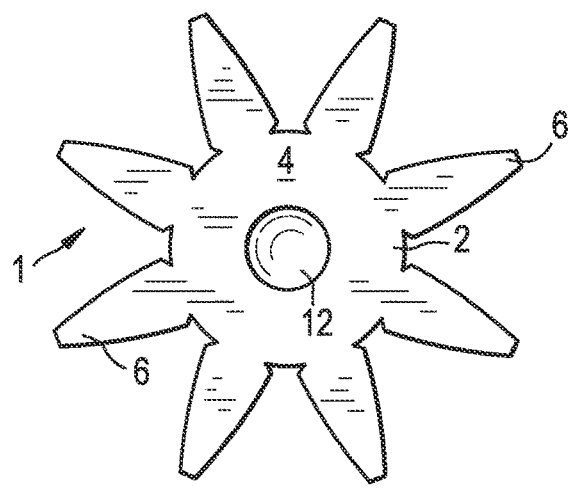
Figure 1C:

FIG. 1(b) shows the basic structure 2 after a protrusion 12 has been formed in the center area of the primary region 4. FIG. 1(c) displays the protrusion 12 in longitudinal section in a plane perpendicular to the plane of FIG. 1(b) and running through the center of the basic structure 2. In the embodiment, the protrusion 12 has an elliptic curvature and is atraumatic, i.e. it is designed as a low-profile tip. It is formed by thermo-setting, which results in a stiffening effect in the center area of the basic structure 2 and stabilizes the primary region 4 of the implant 1. The protrusion 12 facilitates the handling of the implant 1 during surgery, can prevent a tip of a grasping instrument from penetrating the basic structure 2 and causing injury, and minimizes an irritation of the peritoneum.

Figure 1D:
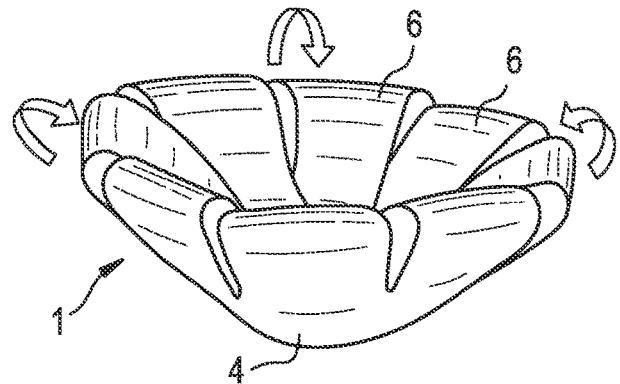

FIG. 1(d) illustrates how the three-dimensional shape of the implant 1 is formed. To this end, the arms 6 are folded back towards the primary region 4, as indicated by the arrows, and the end areas 11 of the arms 6 are fixed to the primary region, e.g. by ultrasonic welding, suturing or gluing (e.g. using poly-p-dioxanone as a glue). (To be precisely, FIG. 1(d) relates to a slight variant of the basic structure 2 of FIGS. 1(a) and (1b), in which the arms 6 are slightly wider.) The protrusion 12 is not visible in FIG. 1(d); it extends to the bottom side, i.e. away from the arms 6.

Figure 2:
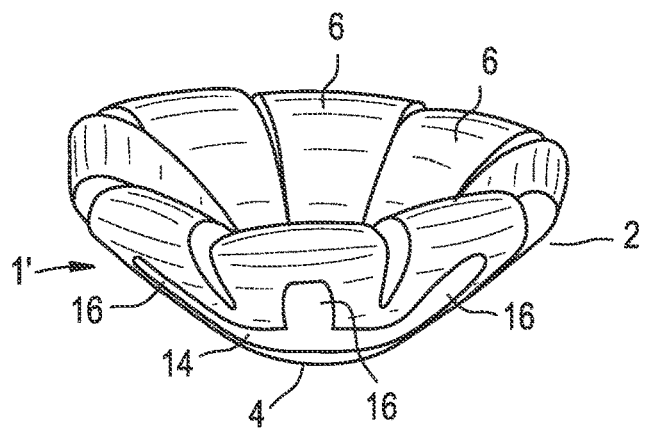

FIG. 2 shows a variant of the implant 1 of FIG. 1, which is designated by 1'. Otherwise, the same reference numerals are used as in FIG. 1.

The implant 1' is reinforced and stiffened by reinforcement elements fixed to the outer face of the basic structure 2 visible in FIG. 2. In the embodiment, the reinforcement elements comprise a circular reinforcement band 14, which encirles the protrusion 12, and radial reinforcement bands 16 extending along part of each arm 6. They are cut from a one-piece blank of poly-p-dioxanone and welded to the basic structure before the arms 6 are folded. An increased stiffness of the implant facilitates its placement during surgery. Poly-p-dioxanone is absorbable so that, after some time, the stiffness imposed by the reinforcement elements disappears. The reinforcement elements can be colored in order to enhance the visibility of the implant during surgery.

Figure 3:
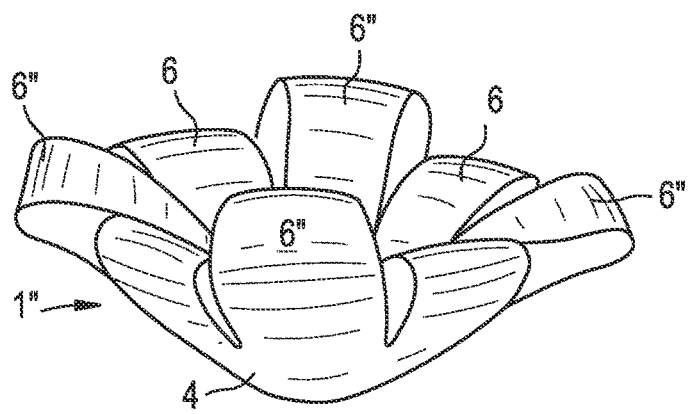

FIG. 3 shows another variant of the implant 1 of FIG. 1, which is designated by 1". Otherwise, the same reference numerals are used as in FIG. 1.

In the implant 1", each second arm 6" is longer than the other arms 6, so that after back-folding the arms and attaching their end areas to the primary region 4, the loops formed by the arms 6" are greater than the loops formed by the arms 6. When, during surgery, the implant 1" is to be fixed to bodily tissue by suturing, the loops of the arms 6" can be preferably used for taking up the sutures.

In the finished implants 1, 1' and 1", as shown in FIGS. 1(d), 2 and 3, the arms 6 and 6' form loops and together act as a plug which can be easily grasped in a surgical procedure and inserted into the defect to be repaired.

Another embodiment of a surgical implant, designated by 20, is illustrated in FIG. 4.

Figure 4A:
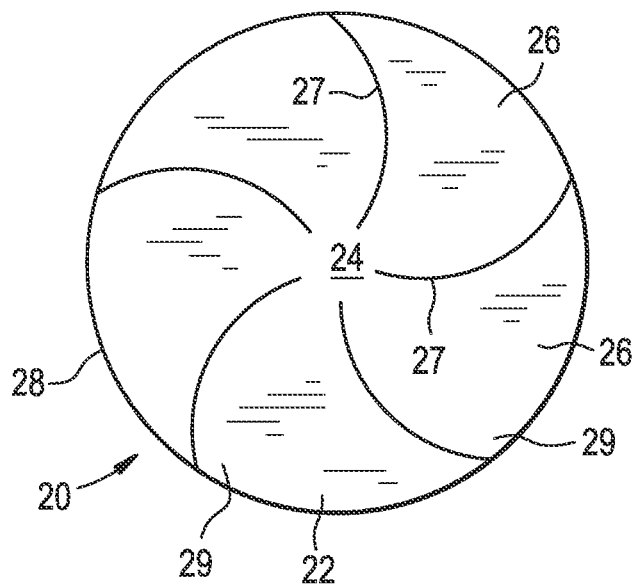

FIG. 4(a) is a plan view of its basic structure 22, which is cut in one piece from mesh material. The basic structure 22 defines a primary region 24 and a total of five arms 26, which are separated by cut lines 27. Since the basic structure is circular and the arms 27 are only separated by the cut lines 27, the free ends 28 of the arms 27 are defined by the circumference line of the circle. After folding back, however, each arm is attached to the primary region 24 in a small peripheral area 29 only.

Figure 4B:
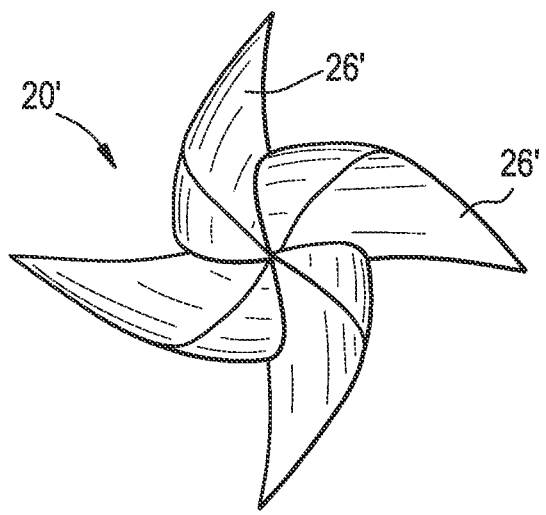
Figure 4C:
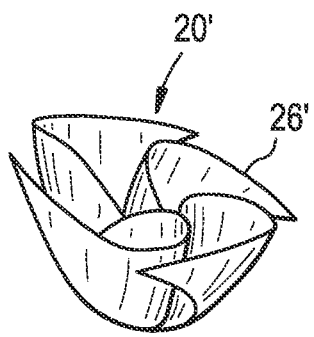

FIG. 4(b) shows the result for the form of the implant after folding back the arms and attachment to the primary region. The implant of FIG. 4(b) is a variant of the implant 20 and designated by 20', because it comprises only four arms 26' instead of five. Moreover, the curvature of the cut lines between the arms 26' is mirror-like compared to the curvature of the cut lines 27 in FIG. 4(a). The arms 26' can be rolled somewhat about the inner parts of the implant 20', which results in the appearance shown in FIG. 4(c).

FIG. 5 displays another embodiment of the surgical implant, here designated by 30.

Figure 5A:
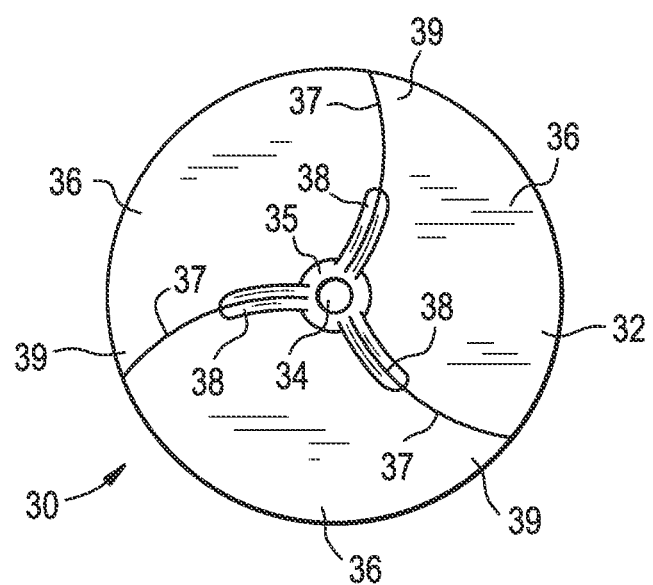

The implant 30 comprises a circular basic structure 32, see FIG. 5(a). Its primary region 34 is reinforced by a circular reinforcement band 35 consisting, in the embodiment, of poly-p-dioxanone. Three arms 36 are separated by curved cut lines 37. In the inner parts of the cut lines 37, the arms are stiffened by redial reinforcement bands 38, which are penetrated by the cut lines 37.

Starting from the state shown in FIG. 5(a), the arms 36 are folded back towards the primary region 34 and are fixed, by means of end areas 39, to the primary region 34. To this end, the poly-p-dioxanone material of the circular reinforcement band 35 is used as a melt-glue.

Figure 5B:
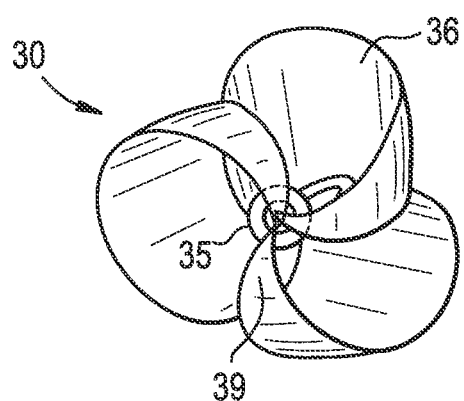

FIG. 5(b) shows the three-dimensional shape of the implant 30. As with the other implants, the loops formed by the arms can be pressed together when the implant is inserted in a hernia defect.

Many examples for suitable materials and compositions of the basic structure, including composite structures, have already been presented further above.

The invention claimed is:

1. A surgical implant adapted for repairing a tissue or muscle wall defect, comprising:
an areal, flat, flexible mesh structure having a pre-formed configuration having a substantially two-dimensional shape, the pre-formed configuration capable of being manipulated into a formed configuration having a substantially three-dimensional shape,
wherein in the pre-formed configuration, said flexible mesh structure comprises a top side, a bottom side, and a center area having a primary region and an outer periphery,
wherein the flexible mesh structure comprises at least two arm members each having a curved shape extending from the outer periphery,
wherein in the pre-formed configuration, each arm member comprises a proximal end adjacent to the outer periphery, a distal end, and an end area between the proximal and the distal end of each arm member, wherein each arm member tapers between its respective proximal and distal end to form the curved shape of the arm member,
wherein in the formed configuration, the distal end of each the arm member is folded inwardly over a top side of its respective proximal end toward the center area such that the distal end of each arm member is directly affixed to the top side of the primary region of the center area of the basic structure such that each arm member forms a loop,
wherein in the formed configuration, the end area of each arm member is the radially outward most portion of the arm member, and
wherein the center area of the flexible mesh structure comprises a permanent curvature formed as a dome-like protrusion in the pre-formed and formed configurations.

2. The surgical implant according to claim 1, characterized in that at least two of the arm members have a different length.

3. The surgical implant according to claim 1, characterized in that the implant is rotationally symmetric with respect to rotations by an angle a about an axis running transversely through the flexible mesh structure wherein n a=360 and n>2.

4. The surgical implant according to claim 1, characterized in that the mesh comprises at least one of the properties selected from the group consisting of: being macro-porous, comprising a warp-knit, comprising a weft-knit, comprising a crochet-knit, comprising a woven fabric, comprising a perforated film, comprising bio-absorbable filaments, comprising non-absorbable filaments, comprising mono-filaments, comprising multi-filaments, comprising tape yarns, and comprising drawn film tapes.

5. The surgical implant according to claim 1, characterized in that the mesh comprises at least one material selected from the group consisting of: polypropylene, poly-p-dioxanone, copolymers of glycolide and lactide, copolymers of glycolide and lactide in the ratio 90:10, copolymers of glycolide and ε-caprolactone, and blends of polyvinylidene fluoride and copolymers of vinylidene fluoride and hexafluoropropene.

6. The surgical implant according to claim 1, characterized in that the flexible mesh structure comprises a composite structure, in which at least one additional layer is added to the mesh.

7. The surgical implant according to claim 6, characterized in that the at least one additional layer comprises a film, wherein the film comprises at least one property selected from the group consisting of the being bio-absorbable, being non-absorbable, and comprising oxidized regenerated cellulose.

8. The surgical implant according to claim 1, characterized in that the flexible mesh structure is made from one piece.

9. The surgical implant according to claim 1, characterized in that the protrusion comprises at least one property selected from the group consisting of: being thermo-formed and having a curved or flattened longitudinal profile.

10. The surgical implant according to claim 1, characterized in that the distal end of the at least one arm, is fixed to the primary region of the flexible mesh structure in one of the ways selected from the group consisting of: welded in the center, welded in an area adjacent to the periphery, welded in intermediate area between the center and the peripheral area, sutured in the center, sutured in an area adjacent to the periphery area, sutured in an intermediate area between the center area and peripheral area, glued in the center area, glued in an area adjacent to the periphery, and glued in an intermediate area between the center and the peripheral area.

11. The surgical implant according to claim 1, characterized by at least one reinforcement element attached to the flexible mesh structure.

12. The surgical implant according to claim 11, characterized in that the at least one reinforcement element comprises at least one property in the group consisting of made as a film, formed as a strip, formed as a rib, arranged concentrically with respect to the center of the flexible mesh structure, arranged radially with respect to the center of the basic flexible mesh structure, laminated to the flexible mesh structure, being absorbable, made from poly-p-dioxanone, and made from a copolymer of glycolide and E-caprolactone, colored.

13. A kit, comprising the surgical implant according to claim 1 and a separate surgical mesh adapted to be placed on top of the tissue or muscle wall defect after the surgical implant has been applied.

14. A method of manufacturing a surgical implant comprising the steps of:
providing an areal, flat, flexible mesh structure having a pre-formed configuration having a substantially two-dimensional shape, the pre-formed configuration capable of being manipulated into a formed configuration having a substantially three-dimensional shape, wherein in the pre-formed configuration, said flexible mesh structure comprises a top side, a bottom side, and a center area having a primary region and an outer periphery, wherein the flexible mesh structure comprises at least two arm members each having a curved shape extending from the outer periphery, wherein in the pre-formed configuration, each arm member comprises a proximal end adjacent to the outer periphery, a distal end, and an end area between the proximal and the distal end of each arm member, wherein each arm member tapers between its respective proximal and distal end to form the curved shape of the arm member, and manipulating the flexible mesh structure from the pre-formed configuration into the formed configuration, such that in the formed configuration, the distal end of each arm member is folded inwardly over a top side of its respective proximal end toward the center area such that the distal end of each arm member is directly affixed to the top side of the primary region of the center area of the basic structure such that each arm member forms a loop, wherein in the formed configuration, the end area of each arm member is the radially outward most portion of the arm member, and wherein the center area of the flexible mesh structure comprises a permanent curvature formed as a dome-like protrusion in the pre-formed and formed configurations.

* * * * *